(12) United States Patent
Kandi et al.

(10) Patent No.: US 8,454,999 B2
(45) Date of Patent: Jun. 4, 2013

(54) SUSTAINED RELEASE COMPOSITIONS OF ALFUZOSIN

(75) Inventors: Chandrashekhar Shriram Kandi, Hingoli (IN); Girish Kumar Jain, Delhi (IN); Amit Gupta, Kanpur (IN)

(73) Assignee: Wockhardt Ltd., Bandra East, Mumbai (IN)

( * ) Notice: Subject to any disclaimer, the term of this patent is extended or adjusted under 35 U.S.C. 154(b) by 0 days.

(21) Appl. No.: 13/475,983

(22) Filed: May 19, 2012

(65) Prior Publication Data

US 2012/0231045 A1     Sep. 13, 2012

Related U.S. Application Data

(62) Division of application No. 11/991,369, filed as application No. PCT/IB2007/000087 on Jan. 12, 2007, now Pat. No. 8,206,742.

(30) Foreign Application Priority Data

| Jan. 12, 2006 | (IN) | 44/MUM/06 |
| Jan. 12, 2006 | (IN) | 45/MUM/06 |
| Jan. 12, 2006 | (IN) | 46//MUM/06 |
| Aug. 31, 2006 | (IN) | 1395/MUM/06 |

(51) Int. Cl.
  *A61K 9/24*     (2006.01)
(52) U.S. Cl.
  CPC ..................................... *A61K 9/209* (2013.01)
  USPC ......................................................... 424/472
(58) Field of Classification Search
  None
  See application file for complete search history.

(56) References Cited

U.S. PATENT DOCUMENTS 5,589,190 A * 12/1996 Andrieu et al. ............... 424/462
6,149,940 A   11/2000 Maggi et al.

FOREIGN PATENT DOCUMENTS

EP    1064938 A1    1/2001
WO   WO9427582 A1  12/1994

* cited by examiner

*Primary Examiner* — Bethany Barham
(74) *Attorney, Agent, or Firm* — Bio Intellectual Property Services LLC (Bio IPS); O. M. (Sam) Zaghmout (57) ABSTRACT

The invention relates to sustained release compositions of alfuzosin or pharmaceutically acceptable salts thereof that include one or more functional layers. The functional layer includes alfuzosin or pharmaceutically acceptable salts thereof and one or more pharmaceutically acceptable hydrophilic and/or hydrophobic rate-controlling polymers.

5 Claims, 6 Drawing Sheets

COMPARATIVE DRUG RELEASE PROFILE
IN 0.01M HCl BUFFER

FIGURE 1: COMPARATIVE DRUG RELEASE PROFILE IN 0.01M HCl BUFFER

FIGURE 4: COMPARATIVE DRUG RELEASE PROFILE IN 0.01M HCl BUFFER

FIGURE 5: COMPARATIVE DRUG RELEASE PROFILE IN pH 6.8 PHOSPHATE BUFFER

FIGURE 6: COMPARATIVE DRUG RELEASE PROFILE IN 0.01M HCl BUFFER

SUSTAINED RELEASE COMPOSITIONS OF ALFUZOSIN

CROSS-REFERENCE TO RELATED APPLICATION

This application is a Division of U.S. application Ser. No. 11/991,369, filed Sep. 16, 2008, now U.S. Pat. No. 8,206,742; which claims a priority of International Application No. PCT. PCT/IB2007/000087, filed on Jan. 12, 2007; an Indian Application No. IN2006MU0001395, filed Aug. 31, 2006; an Indian Application No. IN2006MU0000046, filed Jan. 12, 2006; an Indian Application No. N2006MU0000045, filed Jan. 12, 2006; and an Indian Application No. IN2006MU0000044, filed Jan. 12, 2006. The entire disclosure of these prior applications are hereby incorporated by reference.

FIELD OF THE INVENTION

The field of the invention relates to sustained release compositions of alfuzosin or pharmaceutically acceptable salts thereof that include one or more functional layers. The functional layer includes alfuzosin or pharmaceutically acceptable salts thereof and one or more pharmaceutically acceptable hydrophilic and/or hydrophobic rate-controlling polymers.

BACKGROUND OF THE INVENTION

Alfuzosin is a selective alpha-1 adrenoceptor antagonist that belongs to the chemical class of 4-amino-6,7-dimethoxy-quinazol-2-yl-alkylene diamines. It is commercially available as alfuzosin hydrochloride and marketed as Uroxatral® tablet dosage form. Alfuzosin has a short half-life and shows the characteristic of being absorbed preferentially in the upper part of the gastrointestinal tract and, in particular, being absorbed in the duodenum and the jejunum. Sustained release compositions of alfuzosin provide various advantages over conventional multiple dosing including better patient compliance, reduced fluctuations of plasma drug levels, and reduced toxicity.

Alfuzosin is marketed for the treatment of benign prostatic hyperplasia and, more specifically, for the treatment of the symptoms associated with benign prostatic hyperplasia. Alfuzosin is indicated for the treatment of moderate to severe symptoms of benign prostatic hyperplasia.

U.S. Pat. No. 6,149,940 discloses a preparation of alfuzosin 10 mg once daily composition for oral delivery using a Geomatrix technology. The three-layer tablet described in the patent consists of a hydrophilic active matrix core containing alfuzosin hydrochloride in a single layer supported by two inert, non-functional layers (one swellable layer and one erodible layer) whose functions are to control the hydration and swelling rate of the core, and thereby slow down and linearize the dissolution of the drug. When the tablet comes into contact with gastric juices, it increases considerably in volume and thus remains in the stomach for a longer time. In this manner, most of the drug is absorbed in a controlled manner in the portion of the gastrointestinal tract having the highest capacity for absorption. The alfuzosin is released in zero order from the dosage form developed using this technology.

U.S. Pat. No. 5,589,190 discloses a pharmaceutical composition that includes an alfuzosin core. The core is coated with a coating whose dissolution is pH dependent, which thereby enables the release of alfuzosin to be modulated over the entire length of the digestive tract.

EP 700,285 discloses drug delivery compositions of alpha adrenoceptor blocking agents that have a biphasic drug release profile.

U.S. Pat. No. 4,259,314 discloses a dry pharmaceutical formulation containing a therapeutic agent and a dry carrier that includes hydroxypropyl methylcellulose and hydroxypropyl cellulose.

International (PCT) Publication WO2004037228 discloses sustained release dosage forms of alfuzosin or salts thereof having single functional layers and optionally one or more non-functional layers along with one or more release retarding ingredients.

Several other pharmaceutical compositions comprising alfuzosin have been reported for example, in U.S. Pat. No. 5,589,190; U.S. application Nos. 20060062846; 20060062845; 20060147530; European Patent Nos. 938318 (B1); 673650(B1); 1556014(A1) and International (PCT) Publication Nos. WO2004037228 and WO2006094736.

SUMMARY OF THE INVENTION

In one general aspect there is provided a sustained release formulation that includes one or more functional layers. The functional layer includes alfuzosin or pharmaceutically acceptable salts thereof and one or more pharmaceutically acceptable hydrophilic and/or hydrophobic rate-controlling polymers.

Embodiments of the sustained release formulation may include one or more of the following features. For example, the functional layer may only include hydrophilic and/or hydrophobic rate-controlling polymers. The functional layer may further include one or more pharmaceutically acceptable excipients. The one or more pharmaceutically acceptable excipients may include one or more binders, diluents, and lubricants/glidants.

The sustained release formulation may include a first layer that includes alfuzosin or pharmaceutically acceptable salts thereof and at least one hydrophilic rate controlling polymer, second layer that includes alfuzosin or pharmaceutically acceptable salts thereof and at least one hydrophilic rate controlling polymer and, an optional, third layer that includes one or more hydrophilic rate controlling polymers.

The sustained release formulation may include between about 5% to about 95% of at least one hydrophilic rate-controlling polymer and alfuzosin or pharmaceutically acceptable salts thereof in the first layer. The sustained release formulation may release about 30% or less amount of alfuzosin within first hour and about 50% or more within next 19 hours when the dissolution is measured using USP Type II apparatus at 100 rpm and using 0.01 M hydrochloric acid at 37° C.±2.

The first layer may include alfuzosin or pharmaceutically acceptable salts thereof and less than about 5% of at least one hydrophilic rate controlling polymer and the second layer includes alfuzosin or pharmaceutically acceptable salts thereof and between about 0.5% to about 95% of at least one hydrophilic rate controlling polymer.

The sustained release formulation may release about 20% or less amount of alfuzosin within first hour and about 50% or more within next 19 hours when the dissolution is measured using USP Type II apparatus at 100 rpm and using pH 6.8 phosphate buffer at 37° C.±2.

In another general aspect there is provided a sustained release formulation that includes a first layer that includes alfuzosin or pharmaceutically acceptable salts thereof and between about 0.1% to about 95% of at least one hydrophobic rate controlling polymer, a second layer that includes alfuzosin or pharmaceutically acceptable salts thereof and between about 0.1% to about 95% of at least one rate controlling polymer, and an optional third layer that includes one or more rate-controlling polymers.

The first layer may comprise alfuzosin or pharmaceutically acceptable salts thereof and less than about 0.1% to about 5% of at least one hydrophobic rate controlling polymer and the second layer may comprise alfuzosin or pharmaceutically acceptable salts thereof and about 0.1% to about 95% of at least one rate-controlling polymer.

The sustained release formulation may release about 35% or less amount of alfuzosin within first hour and about 50% or more amount of alfuzosin within next 19 hours when the dissolution is measured using USP Type II apparatus at 100 rpm and using 0.01 M hydrochloric acid at 37° C.±2.

The sustained release formulation may release about 30% or less amount of alfuzosin within first hour and about 50% or more is released within next 19 hours when the dissolution is measured using USP Type II apparatus at 100 rpm and using 0.01 M hydrochloric acid at 37° C.±2.

The sustained release formulation may release about 25% or less amount of alfuzosin within first hour and about 50% or more within next 19 hours when the dissolution is measured using USP Type II apparatus at 100 rpm and using pH 6.8 phosphate buffer at 37° C.±2.

In another general aspect there is provided a sustained release formulation that includes a first layer that includes alfuzosin or pharmaceutically acceptable salts thereof in which rate-controlling polymer is "substantially absent", and the second layer includes alfuzosin or pharmaceutically acceptable salts thereof and about 0.1% to about 95% of at least one rate controlling polymer and, an optional third layer that includes one or more rate-controlling polymers.

The first layer may comprise pregelatinised starch or an equivalent thereof. The sustained release dosage form may have a dissolution profile of about 25% or less in about first hour, about 50% or more in next 19 hours when measured in a USP Type II apparatus at 100 rpm and using 0.01 M hydrochloric acid at 37° C.±2. Alternatively, the sustained release dosage form may have a dissolution of about 25% or less in about first hour, about 50% or more in next 19 hours when measured in a USP Type II apparatus at 100 rpm and using pH 6.8 phosphate buffer at 37° C.±2.

The details of one or more embodiments of the inventions are set forth in the description below. Other features, objects and advantages of the inventions will be apparent from the description and claims.

DETAILED DESCRIPTION OF THE INVENTION

The inventors have found that a sustained release formulation can be effectively made having one or more functional layers. The functional layer may include alfuzosin or pharmaceutically acceptable salts thereof and one or more pharmaceutically acceptable hydrophilic and/or hydrophobic rate-controlling polymers.

The first layer may include alfuzosin or pharmaceutically acceptable salts thereof and at least one hydrophilic rate-controlling polymer in amount of less than about 5% and the second layer may include alfuzosin or pharmaceutically acceptable salts thereof and at least one rate-controlling polymer in amount of about 0.5% to about 95% of the total weight of the layer.

The first layer may include alfuzosin or pharmaceutically acceptable salts thereof in which rate-controlling polymers are substantially absent and subsequent layers may include alfuzosin, at least one rate-controlling polymer and other pharmaceutically acceptable excipients.

A first aspect of the invention provides a sustained release formulation comprising:
  a) a first layer comprising alfuzosin or pharmaceutically acceptable salts thereof and at least one hydrophilic rate controlling polymer;
  b) a second layer comprising alfuzosin or pharmaceutically acceptable salts thereof and at least one hydrophilic rate controlling polymer; and
  c) an optional third layer comprising one or more hydrophilic rate controlling polymers.

Embodiments of the sustained release formulation may include one or more of the following features. For example, the sustained release formulation may include a first layer, a second layer and, an optional third layer, wherein the second layer may include at least one pharmaceutically acceptable diluent and/or lubricant.

The term "alfuzosin" as used herein includes alfuzosin or pharmaceutically acceptable salts thereof.

The sustained release formulation may release about 30% or less amount of alfuzosin is released within first hour and about 50% or more amount of alfuzosin is released within next 19 hours when the dissolution is measured using USP Type II apparatus at 100 rpm and using 0.01 M hydrochloric acid at 37° C.±2.

The sustained release formulation may release about 20% or less amount of alfuzosin is released within first hour and about 50% or more amount of alfuzosin is released within next 19 hours when the dissolution is measured using USP Type II apparatus at 100 rpm and using pH 6.8 phosphate buffer at 37° C.±2.

The multi-layer composition may include at least two functional layers, which include alfuzosin or pharmaceutically acceptable salts thereof. Each functional layer may further comprise at least one rate-controlling polymer.

The multi-layer composition may include an immediate release layer and a sustained release layer. The immediate release layer is characterized by the fact that it may release 80% of the alfuzosin present in the immediate release layer within 15 min when the dissolution is measured using USP Type II apparatus at 100 rpm and using 0.01 M hydrochloric acid at 37° C.±2. The immediate release layer may include the rate-controlling polymer. The percentage of rate controlling polymer can vary between about 5% to about 95% w/w of the total weight of the individual layer.

The sustained release layer of the multi-layer composition may include alfuzosin or pharmaceutically salts thereof and at least one rate controlling polymer. The sustained release layer may release 35% or less amount of alfuzosin within first hour and about 50% or more within next 19 hours when the dissolution is measured using USP Type II apparatus at 100 rpm and using 0.01 M hydrochloric acid at 37° C.±2.

A second aspect of the invention provides a sustained release formulation comprising:

a) a first layer comprising alfuzosin or pharmaceutically acceptable salts thereof and about 0.1% to about 95% of at least one hydrophobic rate controlling polymer;

b) a second layer comprising alfuzosin or pharmaceutically acceptable salts thereof and about 0.1% to about 95% of at least one rate controlling polymer; and c) an optional third layer comprising one or more rate-controlling polymers.

Embodiments of the sustained release formulation may include one or more of the following features. For example, the sustained release formulation may include a first layer, a second layer and, an optional third layer, wherein the second layer may include at least one pharmaceutically acceptable diluent and/or lubricant.

The sustained release formulation may release about 35% or less amount of alfuzosin within first hour and about 50% or more within next 19 hours when the dissolution is measured using USP Type II apparatus at 100 rpm and using 0.01 M hydrochloric acid at 37° C.±2.

The percentage of hydrophobic rate controlling polymer in the first layer can vary between about 0.1% to about 95% w/w of the total weight of the individual layer. In particular, the percentage can be between about 0.1% to about 5% of the weight of the layer. The percentage of rate-controlling polymer in the second layer can vary between about 0.5% to about 95% w/w of the total weight of the individual layer. The rate-controlling polymer present in the second layer can be hydrophilic or hydrophobic. A mixture of hydrophilic and hydrophobic polymer can also be employed effectively.

A third aspect of the invention provides a sustained release formulation comprising:

a) a first layer comprising alfuzosin or pharmaceutically acceptable salt s thereof and less than about 5% of at least one hydrophilic rate controlling polymer;

b) a second layer comprising alfuzosin or pharmaceutically acceptable salt s thereof and 0.5 to 95% of at least one hydrophilic rate controlling polymer; and c) an optional third layer comprising one or more hydrophilic rate controlling polymer.

Embodiments of the sustained release formulation may include one or more of the following features. For example, the sustained release formulation may include a first layer, a second layer and, an optional third layer, wherein the second layer may include at least one pharmaceutically acceptable diluent and/or lubricant.

The sustained release formulation may release about 30% or less amount of alfuzosin within first hour and about 50% or more amount within next 19 hours when the dissolution is measured using USP Type II apparatus at 100 rpm and using 0.01 M hydrochloric acid at 37° C.±2.

The sustained release formulation may release about 25% or less amount of alfuzosin within first hour and about 50% or more within next 19 hours when the dissolution is measured using USP Type II apparatus at 100 rpm and using pH 6.8 phosphate buffer at 37° C.±2.

The percentage of hydrophilic rate controlling polymer in the first layer can vary between about 0.1% to about 5% w/w of the total weight of the individual layer. The percentage of hydrophilic rate controlling polymer in the second layer can vary between about 0.5% to about 95% w/w of the total weight of the individual layer.

A fourth aspect of the invention provides a sustained release formulation comprising:

a) a first layer comprising alfuzosin or pharmaceutically acceptable salts thereof in which rate controlling polymer is "substantially absent";

b) a second layer comprising alfuzosin or pharmaceutically acceptable salts thereof and about 0.1% to about 95% of at least one rate controlling polymer; and c) an optional third layer comprising one or more rate-controlling polymers.

Embodiments of the sustained release formulation may include one or more of the following features. For example, the sustained release formulation may include a first layer, a second layer and, an optional third layer, wherein the first layer may include pregelatinized starch or an equivalent thereof and the second layer may include at least one pharmaceutically acceptable diluent and/or lubricant.

The sustained release formulation may release about 25% or less amount of alfuzosin within first hour and about 50% or more within next 19 hours when the dissolution is measured using USP Type II apparatus at 100 rpm and using 0.01 M hydrochloric acid at 37° C.±2.

In the first layer the rate controlling polymers are "substantially absent". The term "substantially absent" refers to the amount of the rate-controlling polymer, which does not impart any rate controlling function or which does not provide any swelling property to the alfuzosin layer. This functional layer also may include pre-gelatinized starch or an equivalent thereof.

The second functional layer may include at least one rate-controlling polymer. The percentage of rate-controlling polymer in the second layer can vary between about 0.5% to about 95% w/w of the total weight of the individual layer. The rate-controlling polymer present in second layer can be hydrophilic or hydrophobic. A mixture of hydrophilic and hydrophobic polymer can also be employed effectively.

The sustained release dosage form may have a dissolution of about 25% or less in about first hour, about 50% or more in next 19 hours when measured in a USP Type II apparatus at 100 rpm and using 0.01 M hydrochloric acid at 37° C.±2. Alternatively, the sustained release dosage form may have a dissolution of about 25% or less in about first hour, about 50% or more in next 19 hours when measured in a USP Type II apparatus at 100 rpm and using pH 6.8 phosphate buffer at 37° C.±2.

The sustained release dosage form containing alfuzosin or salt thereof includes solid oral dosage forms such as tablets, capsules, granules and pellets.

The multi-layer composition having more than one functional layer can be prepared by dry as well as wet granulation.

The dry granulation comprises preparation of granules corresponding to each functional layer, which are then suitably lubricated and compressed to form multi-layer composition. The composition can be coated to have aesthetic appeal. Such coating can contain a colorant, plasticizer and a polymer.

In turn, the granules corresponding to each functional layer can be prepared by mixing alfuzosin or salt thereof along with rate-controlling polymer and pharmaceutically acceptable excipients. The blend is compacted along with suitable lubricant and sized to provide granules of desired dimensions.

The individual functional layer can have about 0.1 mg to 30 mg of alfuzosin or salts thereof. The first layer can have about 0.1 to 7 mg of alfuzosin or salts thereof and the second layer can have about 3 mg or more of alfuzosin or salts thereof.

The capsule dosage form can contain a composition mentioned above placed in empty capsule shell or granules of drug along with rate controlling polymer and excipient can be filled in the capsule.

The pharmaceutically acceptable rate controlling polymers may be one or more of carbohydrate gum, polyuronic acid salts, cellulose ethers and mixtures thereof. Suitable carbohydrate gums include one or more of xanthan gum, tragacanth gum, gum karaya, guar gum, acacia, gellan, locust bean gum and other carbohydrate gums having similar properties. Suitable polyuronic acid salts include one or more of alkali metal salts of alginic acid or pectic acid and mixtures thereof. Suitable alkali metal salts of alginic acid that may be used include one or more of sodium alginate, potassium alginate, ammonium alginate and other suitable alkali metal salts of alginic acid. Suitable cellulose ethers include one or more of hydroxypropyl methylcellulose, hydroxypropyl cellulose, methylcellulose and hydroxypropyl ethylcellulose.

Optionally, each functional layer may include at least one pharmaceutically acceptable excipient. The pharmaceutically acceptable excipient may include one or more of diluents, disintegrants, lubricants, binders, fillers or glidants. The binder may be one or more of starch, pregelatinized starch, sugars, gums, low molecular weight hydroxypropyl methylcellulose, polyvinyl pyrrolidone and hydroxypropyl cellulose. The lubricant may be one or more of talc, magnesium stearate, calcium stearate, polyethylene glycol, hydrogenated vegetable oils, stearic acid, sodium stearyl fumarate and sodium benzoate. The glidant may be one or both of colloidal silicon dioxide and talc. Suitable coloring or flavoring agents include those approved for use by the United States Food and Drug Administration (FDA) and are well known to those skilled in the art.

The present invention is further illustrated by the following examples which are provided merely to be exemplary of the invention and do not limit the scope of the invention. Certain modifications and equivalents will be apparent to those skilled in the art and are intended to be included within the scope of the present invention.

EXAMPLE 1 AND 2

The composition of the batches is provided in Table 1.
Layer 1: Alfuzosin hydrochloride ranging from 0.1 mg to 7 mg, hydroxypropyl methylcellulose, lactose, hydroxypropyl cellulose, microcrystalline cellulose, aerosil, magnesium stearate, colorant and povidone were passed through ASTM mesh #60 and mixed in a suitable blender. The blend was compacted to get flakes of suitable hardness. The flakes were further sized to get granules of desired dimensions. Lubricant was passed through ASTM mesh #40 and mixed with the granules.

Layer 2: Alfuzosin hydrochloride about 3 mg or more, hydroxypropyl methylcellulose, lactose, hydroxypropyl cellulose, microcrystalline cellulose, aerosil, magnesium stearate and povidone were passed through ASTM mesh #60 and mixed in a suitable blender. The blend was compacted to get flakes of suitable hardness. The flakes were further sized to get granules of desired dimensions. Lubricant was passed through ASTM mesh #40 and mixed with the granules.

Blends of layer 1 and 2 were compressed using suitable tooling to get the bi-layered tablet.

Table 1 provides compositions of the invention.

Table 2 provides the dissolution data of the tablets prepared as per the Formula provided in Table 1. For determination of drug release rate, 0.01M hydrochloric acid buffer in 500 ml of medium using USP Type 2 Apparatus (rpm 100) was used.

Table 3 provides the dissolution data of the tablets prepared as per the Formula provided in Table 1. For determination of drug release rate, pH 6.8 phosphate buffer in 500 ml of medium using USP Type 2 Apparatus (rpm 100) was used.

TABLE 1

| | Example 1 | | Example 2 | |
| --- | --- | --- | --- | --- |
| Ingredient | Layer I Mg/tab | Layer II Mg/tab | Layer I Mg/tab | Layer II Mg/tab |
| Alfuzosin HCl | 5.0 | 5.0 | 2 | 8 |
| HPMC -K100 M CR | 37.5 | 37.5 | — | 60 |
| HPMC -K4 M CR | — | — | 8.0 | — |
| HPC -M | 60.0 | 60.0 | 8 | — |
| Povidone 30 | 7.5 | 7.5 | 10 | 96 |
| Microcrystalline cellulose | 26.5 | 26.5 | 31.69 | 42.4 |
| Talc | 0.5 | 0.5 | 0.25 | 0.8 |
| Magnesium stearate | 1.0 | 1.0 | 0.5 | 1.6 |
| Aerosil | 2.0 | 2.0 | 0.5 | 3.2 |
| Lactose DCL-21 | 10 | 10 | 0.5 | 16 |
| Iron oxide yellow | — | — | 0.06 | — |
| Layer weight (mg) | 150 | 150 | 60.0 | 240 |
| Tablet weight (mg) | 300.0 | | 300.0 | |

TABLE 2

Dissolution data in 0.01M HCl Buffer

| Duration (hrs) | Uroxatral ® % release | Example 1 % release | Example 2 % release |
| --- | --- | --- | --- |
| 0.0 | 0 | 0 | 0 |
| 1.0 | 17 | 14 | 17 |
| 2.0 | 24 | 22 | 26 |
| 4.0 | 35 | 34 | 39 |
| 6.0 | 45 | 45 | 51 |
| 8.0 | 57 | 54 | 61 |
| 10.0 | 67 | 62 | 69 |
| 12.0 | 77 | 68 | 76 |
| 14.0 | 86 | 75 | 82 |
| 16.0 | 93 | 81 | 86 |
| 18.0 | 100 | 84 | 89 |
| 20.0 | 105 | 88 | 92 |

TABLE 3

Dissolution data in pH 6.8 Phosphate Buffer

| Duration (hrs) | Uroxatral ® % release | Example 1 % release | Example 2 % release |
| --- | --- | --- | --- |
| 0.0 | 0 | 0 | 0 |
| 1.0 | 14 | 8 | 14 |
| 2.0 | 20 | 14 | 22 |
| 4.0 | 28 | 22 | 32 |
| 6.0 | 34 | 30 | 42 |
| 8.0 | 40 | 37 | 49 |
| 10.0 | 46 | 44 | 57 |
| 12.0 | 50 | 49 | 63 |
| 14.0 | 57 | 54 | 69 |
| 16.0 | 61 | 59 | 75 |
| 18.0 | 65 | 63 | 79 |
| 20.0 | 70 | 67 | 83 |

Figure 1:
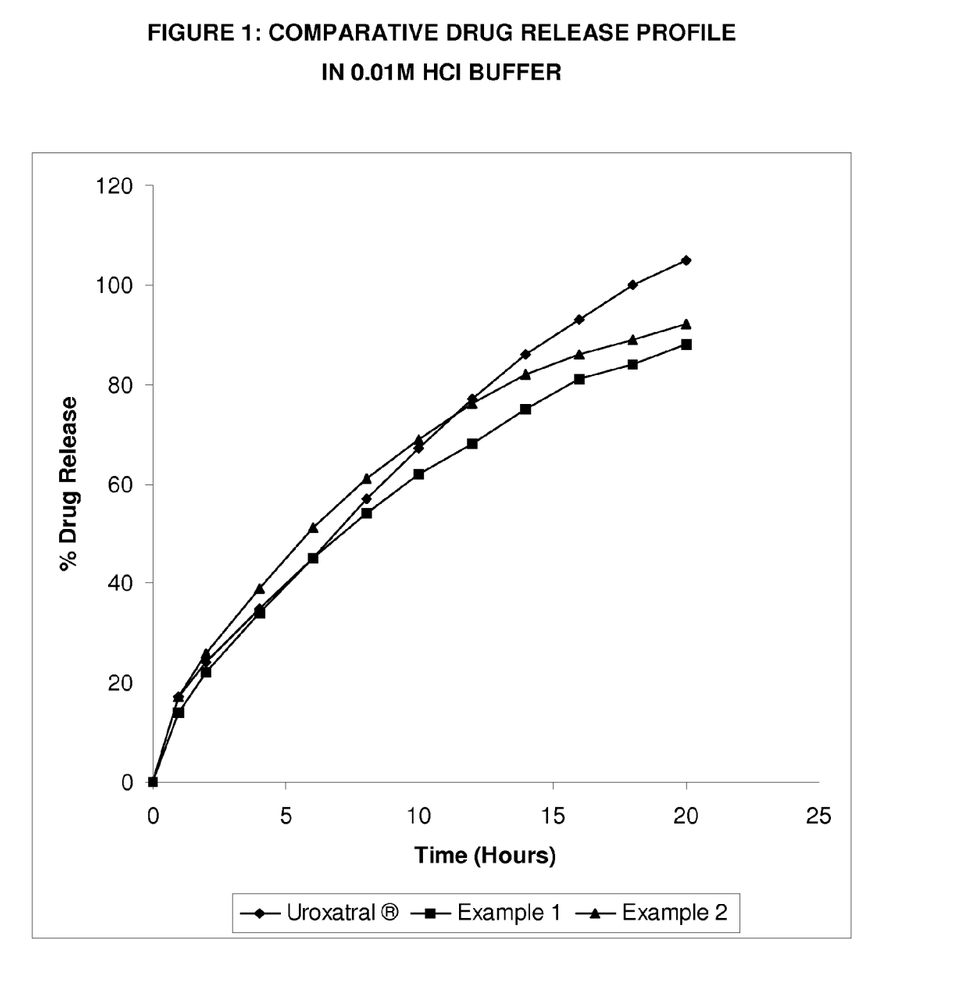
FIG. 1 shows a comparative drug release profile of examples 1 and 2 in 0.1 N HCl buffer.
Figure 2:
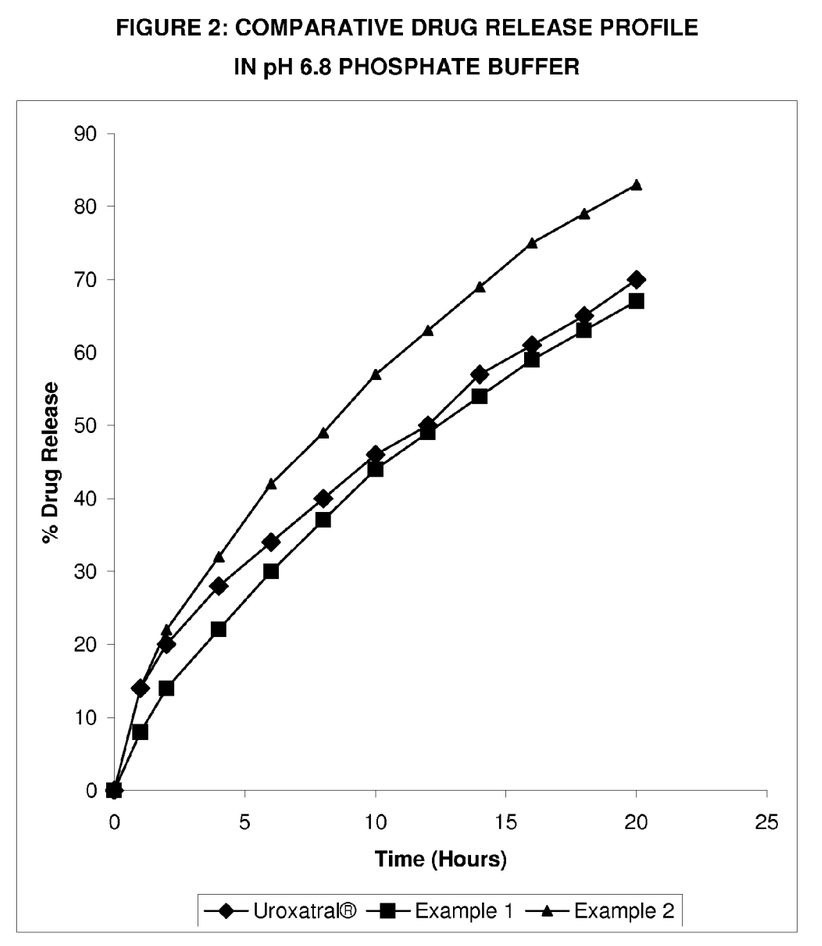
FIG. 2 shows a comparative drug release profile of examples 1 and 2 in pH 6.8 phosphate buffer.

FIG. 1 and FIG. 2 provides comparative drug release profile against Uroxatral® Tablets in acidic and basic media, respectively.

EXAMPLE 3

The composition of the batch is provided in Table 4.

Layer 1: Alfuzosin hydrochloride ranging from 0.1 mg to 7 mg, ethyl cellulose, lactose, microcrystalline cellulose, aerosil, magnesium stearate, colorant and talc were passed through ASTM mesh #60 and mixed in a suitable blender. The blend was compacted to get flakes of suitable hardness. The flakes were further sized to get granules of desired dimensions. Lubricant was passed through ASTM mesh #40 and mixed with the granules.

Layer 2: Alfuzosin hydrochloride about 3 mg or more, hydroxypropyl methylcellulose, lactose, hydroxypropyl cellulose, microcrystalline cellulose, aerosil, magnesium stearate and povidone were passed through ASTM mesh #60 and mixed in a suitable blender. The blend was compacted to get flakes of suitable hardness. The flakes were further sized to get granules of desired dimensions. Lubricant was passed through ASTM mesh #40 and mixed with the granules.

Blends of layer 1 and 2 were compressed using suitable tooling to get the bi-layered tablet.

Table 4 provides compositions of present invention.

Table 5 provides the dissolution data of the tablets prepared as per the Formula provided in Table 4. For determination of drug release rate, 0.01M hydrochloric acid buffer in 500 ml of medium using USP Type 2 Apparatus (rpm 100) was used.

TABLE 4

| | Example 3 | |
|---|---|---|
| Ingredient | Layer I Mg/tab | Layer II Mg/tab |
| Alfuzosin HCl | 1.0 | 9.0 |
| HPMC -K100 M CR | — | 50.0 |
| Ethyl cellulose -7 cps | 3.5 | — |
| HPC -M | — | 80.0 |
| Povidone 30 | — | 10.0 |
| Microcrystalline cellulose | 57.4 | 31.5 |
| Talc | 0.5 | 0.5 |
| Magnesium stearate | 1.0 | 1.0 |
| Aerosil | 1.5 | 3.0 |
| Lactose DCL-21 | 35.0 | 15.0 |
| Iron oxide yellow | 0.1 | — |
| Layer weight (mg) | 100 | 200 |
| Tablet weight (mg) | 300.0 | |

TABLE 5

Dissolution data in 0.01M HCl Buffer

| Duration (hrs) | Uroxatral ® % Release | Example 3 % Release |
|---|---|---|
| 0.0 | 0 | 0 |
| 1.0 | 17 | 27 |
| 2.0 | 24 | 39 |
| 4.0 | 35 | 54 |
| 6.0 | 45 | 65 |
| 8.0 | 57 | 74 |
| 10.0 | 67 | 81 |
| 12.0 | 77 | 86 |
| 14.0 | 86 | 88 |
| 16.0 | 93 | 92 |
| 18.0 | 100 | 93 |
| 20.0 | 105 | 95 |

Figure 3:
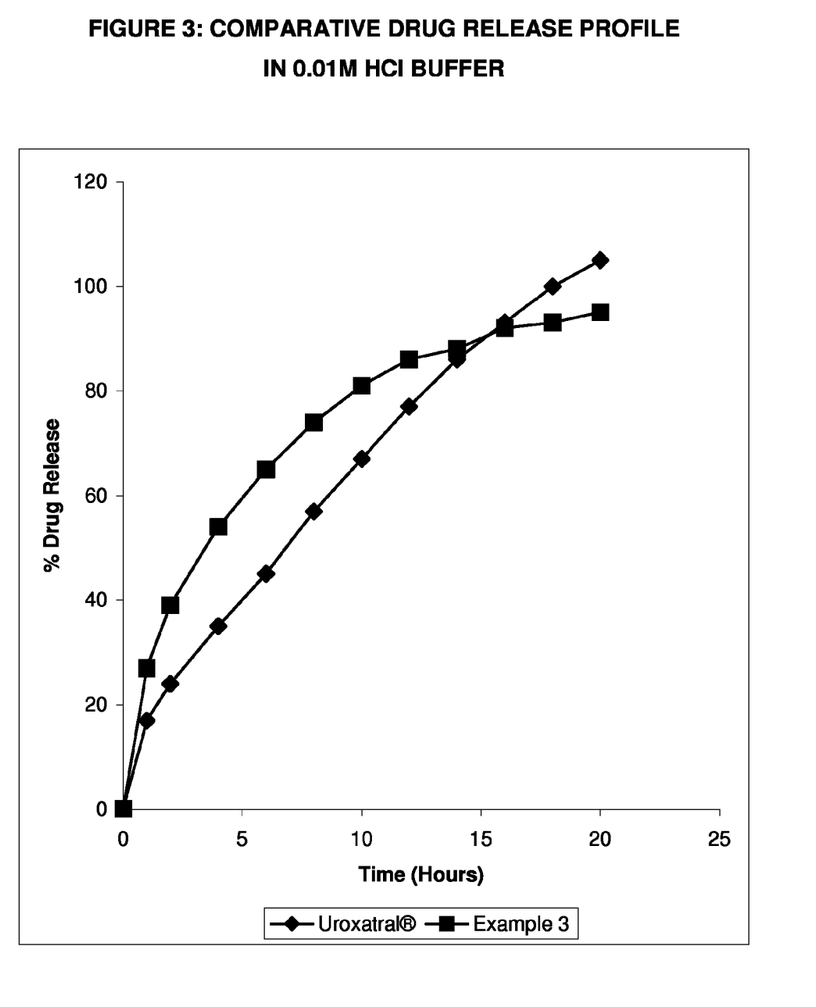
FIG. 3 shows a comparative drug release profile of example 3 in 0.1 N HCl buffer.

FIG. 3 provides comparative drug release profile against Uroxatral® Tablets in acidic media.

EXAMPLE 4 AND 5

The composition of the batches is provided in Table 6.

Layer 1: Alfuzosin hydrochloride ranging from 0.1 mg to 7 mg, hydroxypropyl methylcellulose, lactose, microcrystalline cellulose, aerosil, magnesium stearate, colorant and povidone were passed through ASTM mesh #60 and mixed in a suitable blender. The blend was compacted to get flakes of suitable hardness. The flakes were further sized to get granules of desired dimensions. Lubricant was passed through ASTM mesh #40 and mixed with the granules.

Layer 2: Alfuzosin hydrochloride about 3 mg or more, hydroxypropyl methylcellulose, lactose, hydroxypropyl cellulose, microcrystalline cellulose, aerosil, magnesium stearate and povidone were passed through ASTM mesh #60 and mixed in a suitable blender. The blend was compacted to get flakes of suitable hardness. The flakes were further sized to get granules of desired dimensions. Lubricant was passed through ASTM mesh #40 and mixed with the granules.

Blends of layer 1 and 2 were compressed using suitable tooling to get the bi-layered tablet.

Table 6 provides compositions of the present invention.

Table 7 provides the dissolution data of the tablets prepared as per the Formula provided in Table 6. For determination of drug release rate, 0.01M hydrochloric acid buffer in 500 ml of medium using USP Type 2 Apparatus (rpm 100) was used.

Table 8 provides the dissolution data of the tablets prepared as per the Formula provided in Table 6. For determination of drug release rate, pH 6.8 phosphate buffer in 500 ml of medium using USP Type 2 Apparatus (rpm 100) was used.

TABLE 6

| | Example 4 | | Example 5 | |
|---|---|---|---|---|
| Ingredient | Layer I Mg/tab | Layer II Mg/tab | Layer I Mg/tab | Layer II Mg/tab |
| Alfuzosin HCl | 1.0 | 9.0 | 1.0 | 9.0 |
| HPMC -K100 M CR | 3.0 | 55.0 | — | 50.0 |
| HPMC -K4 M CR | — | — | 3.5 | 0 |
| HPC -M | — | 90.0 | — | 80.0 |
| Povidone 30 | — | 12 | — | 10 |
| Microcrystalline cellulose | 67.61 | 23.55 | 57.4 | 31.5 |
| Talc | 0.5 | 0.75 | 0.5 | 0.5 |
| Magnesium stearate | 1.0 | 1.5 | 1.0 | 1.0 |
| Aerosil | 1.8 | 3.2 | 1.5 | 3.0 |
| Lactose DCL-21 | 15 | 15 | 35 | 15 |
| Iron oxide yellow | 0.09 | — | 0.1 | — |
| Layer weight (mg) | 90.0 | 210.0 | 100.0 | 200.0 |
| Tablet weight (mg) | 300.0 | | 300.0 | |

TABLE 7

Dissolution data in 0.01M HCl Buffer

| Duration (hrs) | Uroxatral ® % release | Example 4 % release | Example 5 % release |
|---|---|---|---|
| 0.0 | 0 | 0 | 0 |
| 1.0 | 17 | 22 | 26 |
| 2.0 | 24 | 29 | 36 |
| 4.0 | 35 | 42 | 51 |
| 6.0 | 45 | 52 | 63 |
| 8.0 | 57 | 61 | 73 |
| 10.0 | 67 | 69 | 80 |
| 12.0 | 77 | 74 | 86 |
| 14.0 | 86 | 79 | 90 |
| 16.0 | 93 | 82 | 93 |

TABLE 7-continued

Dissolution data in 0.01M HCl Buffer

| Duration (hrs) | Uroxatral ® % release | Example 4 % release | Example 5 % release |
|---|---|---|---|
| 18.0 | 100 | 84 | 94 |
| 20.0 | 105 | 86 | 95 |

TABLE 8

Dissolution data in pH 6.8 Phosphate Buffer

| Duration (hrs) | Uroxatral ® % release | Example 4 % release | Example 5 % release |
|---|---|---|---|
| 0.0 | 0 | 0 | 0 |
| 1.0 | 14 | 16 | 19 |
| 2.0 | 20 | 23 | 26 |
| 4.0 | 28 | 31 | 37 |
| 6.0 | 34 | 38 | 46 |
| 8.0 | 40 | 46 | 54 |
| 10.0 | 46 | 52 | 63 |
| 12.0 | 50 | 58 | 67 |
| 14.0 | 57 | 62 | 75 |
| 16.0 | 61 | 66 | 79 |
| 18.0 | 65 | 71 | 82 |
| 20.0 | 70 | 73 | 83 |

Figure 4:
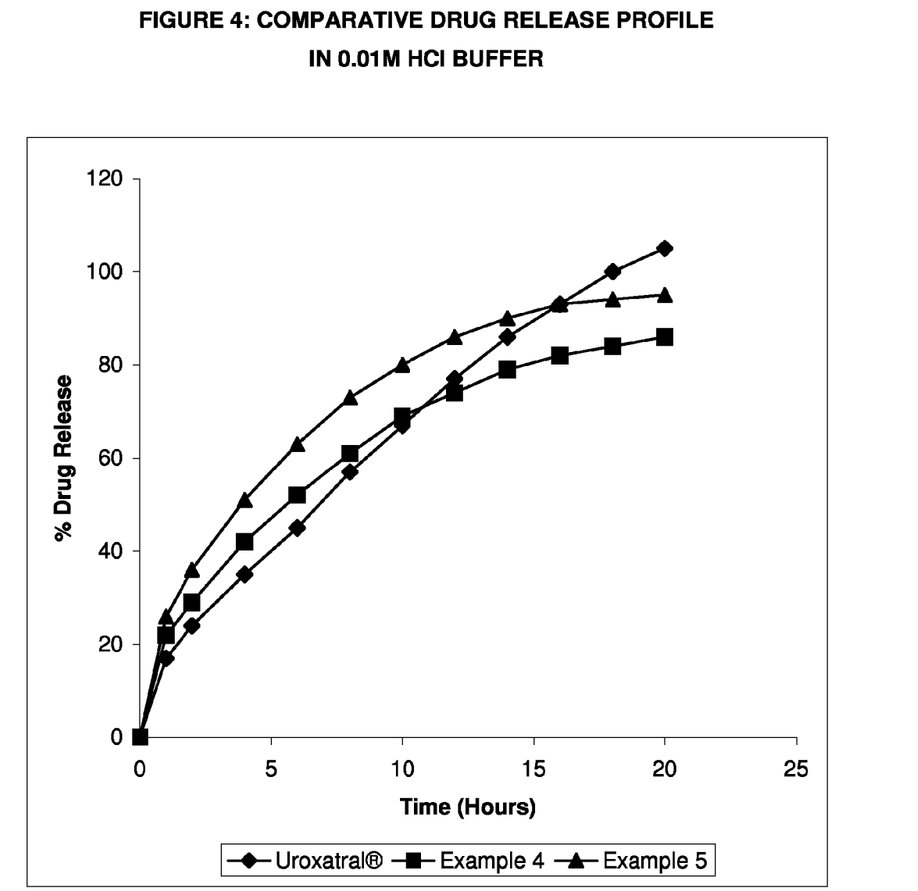
FIG. 4 shows a comparative drug release profile of examples 4 and 5 in 0.1 N HCl buffer.
Figure 5:
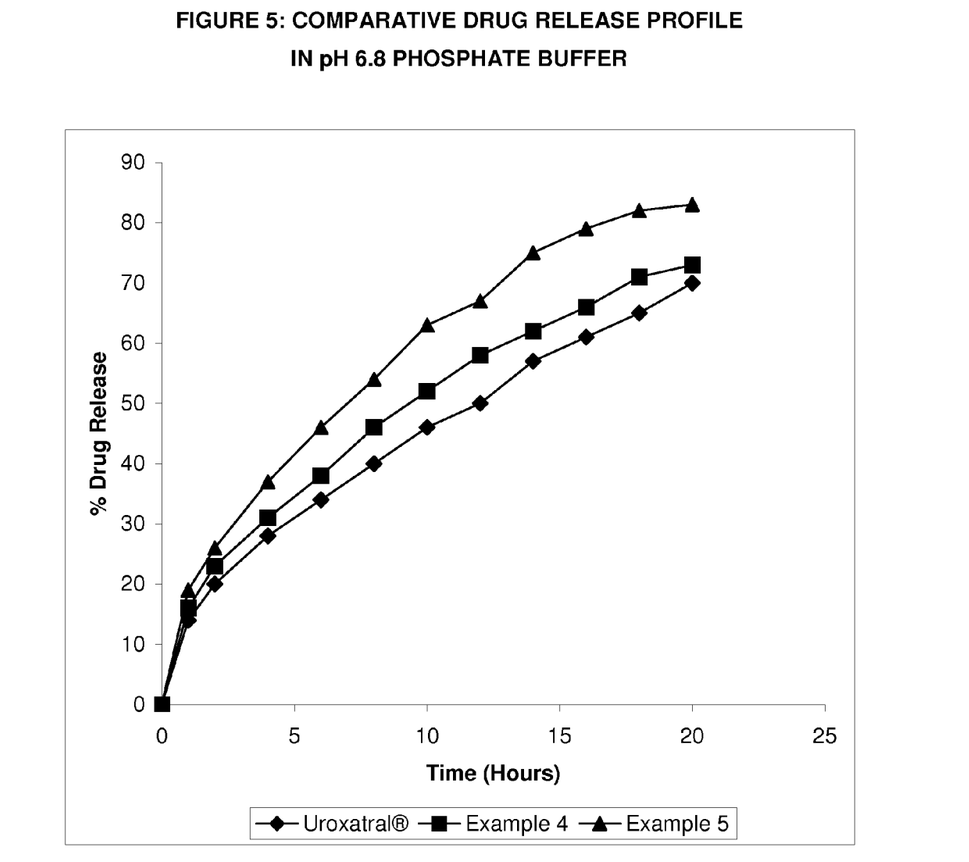
FIG. 5 shows a comparative drug release profile of examples 4 and 5 in pH 6.8 phosphate buffer.

FIG. 4 and FIG. 5 provides comparative drug release profile against Uroxatral® Tablets in acidic and basic media, respectively.

EXAMPLE 6

The composition of the batch is provided in Table 9.

Layer 1: Alfuzosin hydrochloride ranging from 0.1 mg to 7 mg, pregelatinised starch, microcrystalline cellulose, aerosil, magnesium stearate, colorant and talc were passed through ASTM mesh #60 and mixed in a suitable blender. The blend was compacted to get flakes of suitable hardness. The flakes were further sized to get granules of desired dimensions. Lubricant was passed through ASTM mesh #40 and mixed with the granules.

Layer 2: Alfuzosin hydrochloride about 3 mg or more, hydroxypropyl methylcellulose, lactose, hydroxypropyl cellulose, aerosil, magnesium stearate and povidone were passed through ASTM mesh #60 and mixed in a suitable blender. The blend was compacted to get flakes of suitable hardness. The flakes were further sized to get granules of desired dimensions. Lubricant was passed through ASTM mesh #40 and mixed with the granules.

Blends of layer 1 and 2 were compressed using suitable tooling to get the bi-layered tablet.

Table 9 provides compositions of the present invention.

Table 10 provides the dissolution data of the tablets prepared as per the Formula provided in Table 9. For determination of drug release rate, 0.01M hydrochloric acid buffer in 500 ml of medium using USP Type 2 Apparatus (rpm 100) was used.

TABLE 9

| | Example 6 | |
|---|---|---|
| Ingredient | Layer I Mg/tab | Layer II Mg/tab |
| Alfuzosin HCl | 0.5 | 9.5 |
| HPMC -K100 M CR | — | 81.0 |
| HPC-M | — | 147.0 |
| Povidone 30 | — | 14.0 |
| Pregelatinised starch | 9.0 | — |
| Microcrystalline cellulose | 77.55 | — |
| Talc | 0.5 | 1.75 |
| Magnesium stearate | 0.5 | 3.5 |
| Aerosil | 1.5 | 1.75 |
| Lactose DCL-21 | — | 71.50 |
| Iron oxide yellow | 0.45 | — |
| Layer weight (mg) | 90.0 | 330.0 |
| Tablet weight (mg) | 420.0 | |

TABLE 10

Dissolution data in 0.01M HCl Buffer

| Duration (hrs) | Uroxatral ® % Release | Example 6 % Release |
|---|---|---|
| 0.0 | 0 | 0 |
| 1.0 | 17 | 21 |
| 2.0 | 24 | 29 |
| 4.0 | 35 | 42 |
| 6.0 | 45 | 52 |
| 8.0 | 57 | 61 |
| 10.0 | 67 | 68 |
| 12.0 | 77 | 74 |
| 14.0 | 86 | 80 |
| 16.0 | 93 | 84 |
| 18.0 | 100 | 88 |
| 20.0 | 105 | 91 |

Figure 6:
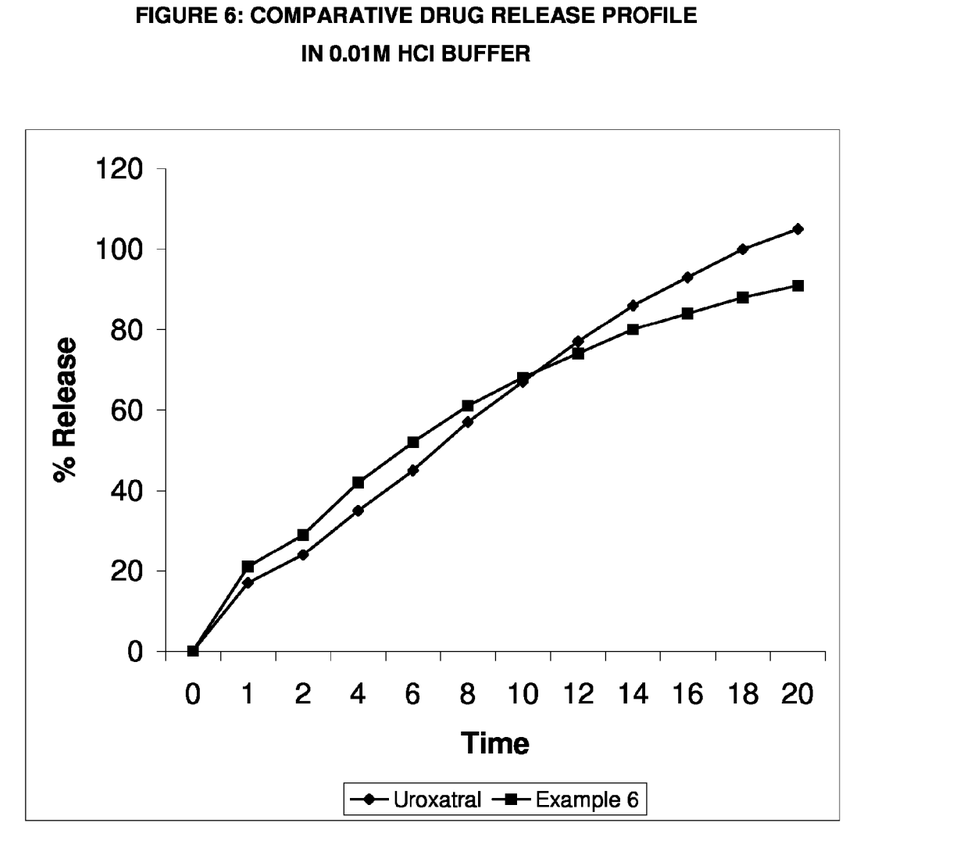
FIG. 6 shows a comparative drug release profile of example 6 in 0.1 N HCl buffer.

FIG. 6 provides comparative drug release profile against Uroxatral® Tablets in acidic media.

While the present invention has been described in terms of its specific embodiments, certain modifications and equivalents will be apparent to those skilled in the art and are intended to be included within the scope of the present invention.

We claim:

1. A sustained release formulation providing a continuous release of alfuzosin comprising:
    a) a first layer comprising alfuzosin or pharmaceutically acceptable salts thereof and about 0.1% to about 5% of at least one hydrophobic rate controlling polymer;
    b) a second layer comprising alfuzosin or pharmaceutically acceptable salts thereof and about 0.1% to about 95% of at least one rate controlling polymer; and
    a) an optional third layer comprising one or more rate-controlling polymers, wherein about 35% or less amount of alfuzosin is released within first hour and about 50% or more within next 19 hours when the dissolution is measured using USP Type II apparatus at 100 rpm and using 0.01 M hydrochloric acid at 37° C.±2° C.

2. The sustained release formulation of claim 1, wherein all the layers further comprise one or more pharmaceutically acceptable excipients.

3. The sustained release formulation of claim 2, wherein the one or more pharmaceutically acceptable excipients comprise one or more of binders, diluents, and lubricants/glidants.

4. The sustained release formulation of claim 1, wherein the hydrophobic rate controlling polymers comprise one or more of ethyl cellulose, cellulose acetate, rosin, shellac, and zein.

5. The sustained release formulation of claim 1, wherein the hydrophobic rate controlling polymer in the first layer is ethyl cellulose.

* * * * *